(12) United States Patent
Haider et al.

(10) Patent No.: US 11,389,784 B2
(45) Date of Patent: Jul. 19, 2022

(54) NEXT GENERATION MODIFIED SILICA MATERIALS FOR INCREASED PERFORMANCE AND INDUSTRIAL APPLICATIONS

(71) Applicant: SABIC Global Technologies B.V., Bergen op Zoom (NL)

(72) Inventors: Muhammad H. Haider, Riyadh (SA); Toseef Ahmed, Riyadh (SA); Khalid Karim, Riyadh (SA)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 16/466,898

(22) PCT Filed: Dec. 14, 2017

(86) PCT No.: PCT/IB2017/057956
§ 371 (c)(1),
(2) Date: Jun. 5, 2019

(87) PCT Pub. No.: WO2018/109718
PCT Pub. Date: Jun. 21, 2018

(65) Prior Publication Data
US 2019/0351400 A1 Nov. 21, 2019

Related U.S. Application Data

(60) Provisional application No. 62/434,724, filed on Dec. 15, 2016.

(51) Int. Cl.
*B01J 23/06* (2006.01)
*B01J 23/02* (2006.01)
(Continued)

(52) U.S. Cl.
CPC ............. *B01J 21/08* (2013.01); *B01J 21/066* (2013.01); *B01J 23/002* (2013.01); *B01J 23/02* (2013.01);
(Continued)

(58) Field of Classification Search
None
See application file for complete search history.

(56) References Cited

U.S. PATENT DOCUMENTS 3,556,725 A    1/1971   Chiola et al. .................... 23/182
4,952,544 A * 8/1990   McCauley ............. B01J 29/049
                                                      502/63
(Continued)

FOREIGN PATENT DOCUMENTS

CN         100355496 C * 12/2007
JP          60202742 A * 10/1985
(Continued)

OTHER PUBLICATIONS

JP-60202742-A, English translation, Oct. 1985, pp. 1-4 (Year: 1985).*
(Continued)

*Primary Examiner* — Medhanit W Bahta
(74) *Attorney, Agent, or Firm* — Norton Rose Fulbright US LLP (57) ABSTRACT

Disclosed are heterostructured silica catalysts (modified Haider heterostructured silica) and methods of their use and preparation. The heterostructured silica catalysts include a transition metal, an alkaline earth metal oxide, and silica, wherein the transition metal, the alkaline earth metal from the metal oxide thereof, and silicon (Si) from silica are each present in the crystal lattice structure of the catalyst. The catalyst can have application in, e.g., the hydrogenation of carbon monoxide.

6 Claims, 3 Drawing Sheets

(51) Int. Cl.

| | |
|---|---|
| *B01J 21/06* | (2006.01) |
| *B01J 21/08* | (2006.01) |
| *B01J 23/00* | (2006.01) |
| *B01J 29/88* | (2006.01) |
| *B01J 37/02* | (2006.01) |
| *B01J 37/03* | (2006.01) |
| *B01J 37/08* | (2006.01) |
| *C07C 1/04* | (2006.01) |

(52) U.S. Cl.
CPC ............... *B01J 23/06* (2013.01); *B01J 29/88* (2013.01); *B01J 37/0236* (2013.01); *B01J 37/031* (2013.01); *B01J 37/08* (2013.01); *C07C 1/044* (2013.01)

(56) References Cited

U.S. PATENT DOCUMENTS

| | | | |
|---|---|---|---|
| 5,019,293 A | 5/1991 | Burlitch | 252/313.1 |
| 5,153,031 A | 10/1992 | Burlitch | 427/226 |
| 2004/0106517 A1 | 6/2004 | Dlamini et al. | 502/326 |
| 2009/0111684 A1 | 4/2009 | Demirel et al. | 502/158 |

FOREIGN PATENT DOCUMENTS

| | | | | |
|---|---|---|---|---|
| JP | 2005246372 A | * | 9/2005 | |
| JP | 2013014451 A | * | 1/2013 | |
| WO | WO-2016011240 A1 | * | 1/2016 | ......... B01J 23/8946 |

OTHER PUBLICATIONS

Translation of Patent No. CN100355496C, Dec. 19, 2007, p. 1-7 (Year: 2007).*

Rhodes, C. N. et al. "Autotransformation and Ageing of Acid-treated Montmorillonite Catalysts: A Solid-state 27Al NMR Study" J. Chem. Soc. Faraday Trans., 1995, 91(6), 1031-1035 (Year: 1995).*

Jacobs, A. P. et al. "Characterization of Reduced Natural Garnierite and Its Catalytic Activity for Carbon Monoxide Hydrogenation" J. Cat. 64, 251-259 (1980) (Year: 1980).*

Chatterjee, M. et al. "Hydrothermal synthesis and characterization of copper containing crystalline silicate mesoporous materials from gel mixture" Applied Clay Science 25 (2004) 195-205 (Year: 2004).*

Hayashi, Y. et al. "Experimental and computational studies of the roles of MgO and Zn in talc for the selective formation of 1,3-butadiene in the conversion of ethanol" Phys. Chem. Chem. Phys., 2016, 18, 25191, Published online Aug. 16, 2016 (Year: 2016).*

JP-2013014451-AJP-2005246372-A, Sep. 2005 (Year: 2005).*

JP-2013014451-A, English translation, Jan. 2013 (Year: 2013).*

Sirotkina, E. et al. "X-ray single-crystal and Raman study of (Na0.86Mg0.14)(Mg0.57Ti0.43)Si2O6, a new pyroxene synthesized at 7 GPa and 1700° C." Phys Chem Minerals (2016) 43:731-738 (Year: 2016).*

Beck et al. "A New Family of Mesoporous Molecular Sieves Prepared with Liquid Crystal Templates", J. Am. Chem. Soc., 114, 10834-10843 (1992).

Cai et al. "Dilute Solution Routes to Various Controllable Morphologies of MCM-41 Silica with a Basic Medium." Chem. Mater., 13, 2, (2001) 258-263.

Corma et al. "Lewis Acids: From Conventional Homogenous to Green Homogenous and Heterogenous Catalysis." Chem. Rev. 103 (2003) 4307-4366.

Davidson, Anne. "Modifying the walls of mesoporous silicas prepared by supramolecular-templating." Curr. Opin. Colloid Interface Sci., 7, 1-2, (2002) 92-106.

Di Renzo et al. "Textural control of micelle-templated mesoporous silicates: the effects of co-surfactants and alkalinity." Micropor. Mesopor. Mater., 28, 3, (1999) 437-446.

International Search Report and Written Opinion from PCT/IB2017/057956 dated Mar. 22, 2018, 13 pages.

Lin et al., "Counterion Effect in Acid Synthesis of Mesoporous Silica Materials", J. Phys. Chem. B, 104, 7885-7894 (2000).

Liu et al., "Calcein-functionalized Fe3O4@SiO2 nanoparticles as a reusable fluorescent nanoprobe for copper(II) ion", Microchim Acta, 182: 547-555, 2015.

Prieto et al. "Towards stable catalysts by controlling collective properties of supported metal nanoparticles." Nature Materials 12 (2013) 34-39.

Sudsakorn et al. "Preparation of Attrition-Resistant Spray-Dried Fe Fischer-Tropsch Catalysts Using Precipitated $SiO_2$." Ind. Eng. Chem. Res.

Tanev et al. "Mesoporous Silica Molecular Sieves Prepared by Ionic and Neutral Surfactant Templating: A Comparison of Physical Properties." Chem. Mater., 8, 8, (1996) 2068-2079.

Thomas, John Meurig. "Handbook of Heterogenous Catalysis." Angew. Chem. Int. Ed. 48 (2009) 3390-3391.

White et al. "Supported metal nanoparticles on porous materials. Methods and applications." Chem. Soc. Rev., 38 (2009) 481-494.

* cited by examiner

NEXT GENERATION MODIFIED SILICA MATERIALS FOR INCREASED PERFORMANCE AND INDUSTRIAL APPLICATIONS

CROSS REFERENCE TO RELATED APPLICATIONS

This application is a national phase application under 35 U.S.C. § 371 of International Application No. PCT/IB2017/057956 filed Dec. 14, 2017, which claims priority to U.S. Provisional Patent Application No. 62/434,724 filed Dec. 15, 2016. The entire contents of each of the above-referenced disclosures is specifically incorporated by reference herein without disclaimer.

FIELD OF INVENTION

The present invention relates to heterostructured silica catalysts and uses thereof. More specifically, the present invention relates to heterostructured silica catalysts including a transition metal, an alkaline earth metal oxide, and silica, wherein the transition metal, the alkaline earth metal from the metal oxide thereof, and silicon (Si) from silica are each present in the crystal lattice structure of the catalyst.

BACKGROUND OF THE INVENTION

Silica containing materials play a pivotal role in many scientific industries including refining, petrochemical, specialty chemicals, biochemical, etc. This is due in part to a range of unique properties found in silica including high surface area, chemical, thermal, and mechanical stabilities, uniformly ordered pore distribution assisting substrate diffusion, and high adsorption tendencies. These properties of silica materials can vary based on the precursors used in their preparation, such as choosing between sodium silicate and a tetraalkyl orthosilicate, or by manipulating synthesis parameters including pH, temperature, reaction duration, additives in the reaction mixture, degree of condensation of poly silica etc.

Considerable effort has been focused on preparing silica materials. By way of example, U.S. Pat. No. 5,153,031 to Burlitch et al., describes stable magnesium containing silicate sols produced from solutions of silicon alkoxide, magnesium alkoxide, and optionally aluminum alkoxide followed by oxidation with a peroxy compound to produce silica-based fibers. U.S. Pat. No. 5,019,293 to Burlitch et al. describes a magnesium aluminosilicate sol that can be reacted with HF to produce a magnesium fluoride silicate sol for use as ceramic coatings. In yet another example, Liu et al ("Calcein-functionalized $Fe_3O_4$@$SiO_2$ nanoparticles as a reusable fluorescent nanoprobe for copper(II) ion", *Microchim Acta*, 2015, 182, pp. 547-555) describes the preparation of silica supported $Fe_3O_4$ nanoparticles for nanoprobes.

Silica sols can be used to make silica supports for catalysts and other materials. These silica-based supports suffer in that they have the catalytically active metals deposited in the pores of the silica support, deposited on the surface of the support, and/or unevenly distributed in the silica matrix.

SUMMARY OF THE INVENTION

A discovery has been made that provides a solution to metal-containing silica materials. The discovery is premised on forming heterostructured silica catalysts having a uniform single crystal structure with silicon (Si), catalytically active metal, and an alkaline earth metal oxide each present in the crystal lattice structure. The catalysts of the present invention can be referred to as MHH—$SiO_2$ (i.e., Modified Haider Heterostructured $SiO_2$) catalysts or materials. It is believed that the MHH—$SiO_2$ catalysts of the present invention obtain their uniform single crystal structure by first forming a polycondensed silica having an external network of alkaline earth metal atoms (e.g., magnesium (Mg)) from a silicon containing organic template (e.g., tetraalkyl orthosilicate). Once formed, a catalytically active transition metal(s) (e.g., iron (Fe)) can be deposited the polycondensed silica structure. Without wishing to be bound by theory, it is believed that once the organic template is removed, the active metal(s) migrates to the support center in a systematic pattern to obtain a uniform and uniquely structured MHH—$SiO_2$ material. In particular, the catalytically active metal, silicon (Si), and an alkaline earth metal atom are each present in the crystal lattice structure. Non-limiting advantages of the MHH—$SiO_2$ materials of the present invention include uniform surface morphology and high stability at increased temperatures over long durations. Further, the MHH—$SiO_2$ materials/catalysts of the present invention can avoid the issues seen with conventional silica-based materials such as having catalytically active metals deposited in the pores of the silica and/or unevenly distributed in the silica matrix. Thus, the materials of the present invention can have applications in a wide variety of industries, including, for example, the chemical industry (e.g., catalyst for chemical reactions such as, but not limited to, a hydrogenation of carbon monoxide reaction).

Embodiments of the present invention describe a heterostructured silica catalyst. The heterostructured silica catalyst can include a transition metal, an alkaline earth metal oxide, and silica, wherein the transition metal, the alkaline earth metal from the metal oxide thereof, and silicon (Si) from silica are each present in the crystal lattice structure of the catalyst. The catalyst can be monometallic, bimetallic, trimetallic, or tetrametallic. In one aspect, the heterostructured silica catalyst can include 0.1 to 10 wt. % of the transition metal, 10 to 20 wt. % of the alkaline earth metal from the metal oxide thereof, and 20 to 40 wt. % of silicon (Si) from silica, based on the total weight of the catalyst. In another aspect, the heterostructured silica includes a weight ratio of silicon (Si) from silica to alkaline earth metal from the metal oxide thereof that is from 0.5:1 to 5:1, preferably from 1:1 to 3:1. In some instances, the transition metal can be one or more of iron (Fe), nickel (Ni), copper (Cu), zinc (Zn), aluminum (Al), zirconium (Zr), or titanium (Ti), preferably Fe. In other instances, the alkaline earth metal oxide can be one or more of magnesium oxide (MgO), calcium oxide (CaO), barium oxide (BaO), or strontium (SrO), preferably magnesium oxide (MgO).

Other embodiments are drawn to a method of preparing the heterostructured silica catalysts of the present invention. The method can include: (a) subjecting an aqueous solution comprising an alkaline earth metal precursor and a tetraalkyl orthosilicate to conditions sufficient to form a polycondensed silica having an external network of alkali earth metal atoms; (b) adding a transition metal precursor material to the aqueous solution under conditions to incorporate transition metal atoms into the polycondensed silica; (c) forming a solid material from the polycondensed silica; and (d) drying and calcining the solid material to form a heterostructured silica catalyst comprising a transition metal, an alkaline earth metal oxide, and silica, wherein the transition metal, the alkaline earth metal from the metal oxide thereof, and silicon (Si) from silica are each present in the crystal lattice structure of the catalyst. The aqueous solution from step (a) can include from 10 to 100% water. In one aspect, the aqueous solution from step (a) can include an alcohol, preferably ethanol, propanol, or butanol. In other aspects of the method, step (a) can include forming an alkaline earth metal precursor solution, heating the solution to a temperature ranging from room temperature (i.e., about 15 to about 30° C., preferably about 20 to 25° C.) to 95° C., preferably from 40 to 70° C., and then adding tetraalkyl orthosilicate to the solution. The molar ratio of tetraalkyl orthosilicate to alkaline earth metal precursor can be 0.5:1 to 6:1, preferably 1:1 to 4:1. In preferred aspects, the tetraalkyl orthosilicate is tetraethyl orthosilicate (TEOS). The molar ratio of alkaline earth metal precursor to transition metal precursor from step (b) can be 5:1 to 50:1, preferably 20:1 to 30:1. In some instances, the solid material from step (c) can be obtained by adding a precipitating agent, wherein the precipitating agent is one or more of ammonium hydroxide ($NH_4OH$), ammonium carbonate [$(NH_4)_2CO_3$], ammonium bicarbonate ($NH_4HCO_3$), sodium carbonate ($Na_2CO_3$), potassium carbonate ($K_2CO_3$), sodium bicarbonate ($NaHCO_3$), or potassium bicarbonate ($KHCO_3$), preferably $NH_4OH$. In other instances, the precipitating agent has a concentration from 1M to 10M of precipitation agent in water. Another feature of the current invention involves calcination of the heterostructured silica catalyst and the calcination from step (d) can include heating at a temperature from 250 to 800° C.

Another embodiment concerns a method of using the heterostructured silica catalyst of the present invention in a chemical reaction, such as in a hydrogenation of carbon monoxide reaction. In one non-limiting aspect, the reaction can include: 0.1 to 5 grams of the heterostructured silica catalyst; a feed stream comprising synthesis gas ($CO/H_2$) at a weight hourly space velocity (WHSV) of 1000 to 2500; a temperature of 200 to 500° C.; and/or a pressure of 0 to 15 bar. The method can also include producing a product stream that can include methane, olefins, paraffins, and/or carbon dioxide. Under the above conditions, the carbon monoxide conversion can be 70 to 78% at 300° C., 67 to 80% at 325° C., and 14 to 53% at 350° C. The selectivity of methane can be 11 to 28%, the selectivity of olefins can be 24 to 41%, the selectivity of paraffins can be 13 to 21%, and the selectivity of carbon dioxide can be 13 to 41%, based on a reaction mass balance of 95±5%.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and/or packages of compositions of the invention can be used to achieve methods of the invention.

The following includes definitions of various terms and phrases used throughout this specification.

The term "catalyst" means a substance which alters the rate of a chemical reaction. "Catalytic" or "catalytically active" means having the properties of a catalyst.

The term "about" or "approximately" are defined as being close to as understood by one of ordinary skill in the art. In one non-limiting embodiment, the terms are defined to be within 10%, preferably within 5%, more preferably within 1%, and most preferably within 0.5%.

The term "substantially" and its variations are defined to include ranges within 10%, within 5%, within 1%, or within 0.5%.

The terms "wt. %", "vol. %", or "mol. %" refers to a weight, volume, or molar percentage of a component, respectively, based on the total weight, the total volume of material, or total moles, that includes the component. In a non-limiting example, 10 grams of component in 100 grams of the material is 10 wt. % of component.

The use of the words "a" or "an" when used in conjunction with any of the terms "comprising," "including," "containing," or "having" in the claims, or the specification, may mean "one," but it is also consistent with the meaning of "one or more," "at least one," and "one or more than one."

The terms "inhibiting" or "reducing" or "preventing" or "avoiding" or any variation of these terms, when used in the claims and/or the specification includes any measurable decrease or complete inhibition to achieve a desired result.

The term "effective," as that term is used in the specification and/or claims, means adequate to accomplish a desired, expected, or intended result.

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The catalysts of the present invention can "comprise," "consist essentially of," or "consist of" particular ingredients, components, compositions, etc. disclosed throughout the specification. With respect to the transitional phase "consisting essentially of," in one non-limiting aspect, a basic and novel characteristic of the catalysts of the present invention are a heterostructured material having a catalytically active metal, silicon (Si), and an alkaline earth metal each present in the crystal lattice structure of the catalyst.

In the context of the present invention, 20 embodiments are now described. Embodiment 1 is a heterostructured silica catalyst. The heterostructured silica catalyst includes a transition metal, an alkaline earth metal oxide, and silica, wherein the transition metal, the alkaline earth metal from the metal oxide thereof, and silicon (Si) from silica are each present in the crystal lattice structure of the catalyst. Embodiment 2 is the heterostructured silica catalyst of embodiment 1, containing 0.1 to 10 wt. % of the transition metal, 10 to 20 wt. % of the alkaline earth metal from the metal oxide thereof, and 20 to 40 wt. % of silicon (Si) from silica, based on the total weight of the catalyst. Embodiment 3 is the heterostructured silica catalyst of any of embodiments 1 to 2, wherein the weight ratio of silicon (Si) from silica to alkaline earth metal from the metal oxide thereof is from 0.5:1 to 5:1, preferably from 1:1 to 3:1. Embodiment 4 is the heterostructured silica catalyst of any of embodiments 1 to 3, wherein the transition metal is one or more of iron (Fe), nickel (Ni), copper (Cu), zinc (Zn), aluminum (Al), zirconium (Zr), or titanium (Ti), preferably Fe. Embodiment 5 is the heterostructured silica catalyst of any of embodiments 1 to 4, wherein the alkaline earth metal oxide is one or more of magnesium oxide (MgO), calcium oxide (CaO), barium oxide (BaO), or strontium (SrO), and preferably magnesium oxide (MgO).

Embodiment 6 is a method of preparing a heterostructured silica catalyst. The method of preparing a heterostructured silica catalyst includes the steps of (a) subjecting an aqueous solution containing an alkaline earth metal precursor and an tetraalkyl orthosilicate to conditions sufficient to form a polycondensed silica having an external network of alkali earth metal atoms; (b) adding a transition metal precursor material to the aqueous solution under conditions to incorporate transition metal atoms into the polycondensed silica; (c) forming a solid material from the polycondensed silica; and (d) drying and calcining the solid material to form a heterostructured silica catalyst containing a transition metal, an alkaline earth metal oxide, and silica, wherein the transition metal, the alkaline earth metal from the metal oxide thereof, and silicon (Si) from silica are each present in the crystal lattice structure of the catalyst. Embodiment 7 is the method of embodiment 6, wherein the aqueous solution from step (a) contains from 10 to 100% water. Embodiment 8 is the method of any of embodiments 6 to 7, wherein the aqueous solution from step (a) contains an alcohol, preferably ethanol, propanol, or butanol. Embodiment 9 is the method of any of embodiments 6 to 8, wherein step (a) includes forming an alkaline earth metal precursor solution; heating the solution to a temperature ranging from 15° C. to 95° C., preferably from 40° C. to 70° C.; and adding tetraalkyl orthosilicate to the solution. Embodiment 10 is the method of embodiment 9, wherein the molar ratio of tetraalkyl orthosilicate to alkaline earth metal precursor is 0.5:1 to 6:1, preferably 1:1 to 4:1. Embodiment 11 is the method of embodiment 10, wherein the tetraalkyl orthosilicate is tetraethyl orthosilicate (TEOS). Embodiment 12 is the method of any of embodiments 6 to 11, wherein the molar ratio of alkaline earth metal precursor to transition metal precursor from step (b) is 5:1 to 50:1. Embodiment 13 is the method of embodiment 12, wherein the molar ratio is 20:1 to 30:1. Embodiment 14 is the method of any of embodiments 6 to 13, wherein the solid material from step (c) is obtained by adding a precipitating agent, wherein the precipitating agent is one or more of ammonium hydroxide ($NH_4OH$), ammonium carbonate [$(NH_4)_2CO_3$], ammonium bicarbonate ($NH_4HCO_3$), sodium carbonate ($Na_2CO_3$), potassium carbonate ($K_2CO_3$), sodium bicarbonate ($NaHCO_3$), or potassium bicarbonate ($KHCO_3$), preferably $NH_4OH$. Embodiment 15 is the method of embodiment 14, wherein the precipitating agent has a concentration from 1M to 10M of precipitation agent in water. Embodiment 16 is the method of any of embodiments 6 to 15, wherein the calcination from step (d) contains heating at a temperature from 250 to 800° C.

Embodiment 17 is a method of using the heterostructured silica catalyst of any of embodiments 1 to 6 in a hydrogenation of carbon monoxide reaction. Embodiment 18 is the method of embodiment 17, wherein the hydrogenation of carbon monoxide reaction includes 0.1 to 5 grams of the heterostructured silica catalyst; a feed stream containing synthesis gas ($CO/H_2$) at a weight hourly space velocity (WHSV) of 1000 to 2500; a temperature of 200 to 500° C.; and a pressure of 0 to 15 bar. Embodiment 19 is the method of embodiment 18, wherein the carbon monoxide conversion is 70 to 78% at 300° C., 67 to 80% at 325° C., and 14 to 53% at 350° C. Embodiment 20 is the method of any of embodiments 17 to 19, further including the step of producing methane, olefins, paraffins, and carbon dioxide, wherein the selectivity of methane is 11 to 28%, the selectivity of olefins is 24 to 41%, the selectivity of paraffins is 13 to 21%, and the selectivity of carbon dioxide is 13 to 41%, based on a reaction mass balance of 95±5%.

Other objects, features and advantages of the present invention will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description. In further embodiments, features from specific embodiments may be combined with features from other embodiments. For example, features from one embodiment may be combined with features from any of the other embodiments. In further embodiments, additional features may be added to the specific embodiments described herein.

BRIEF DESCRIPTION OF THE DRAWINGS

For a more complete understanding, reference is now made to the following descriptions taken in conjunction with the accompanying drawings.

DETAILED DESCRIPTION OF THE INVENTION

The catalysts of the present invention offer a solution to the problems associated with currently available silica supported catalysts. The solution is premised on forming a uniform and uniquely heterostructured $SiO_2$ material (e.g., MHH—$SiO_2$ material) with an active metal, an alkaline earth metal, and silicon (Si) present in the crystal lattice structure. The resulting catalysts of the present invention can offer non-limiting advantages ranging from increased conversion, increased selectivity, lower catalyst deactivation rates, and/or robust thermal stability in for example, catalyzing the production of methane, olefins, paraffins, and carbon dioxide from syngas (e.g., $H_2/CO$).

These and other non-limiting aspects of the present invention are discussed in further detail in the following sections with reference to the Figures.

A. Heterostructured Silica Catalysts

Embodiments herein describe heterostructured silica catalysts and methods of making and using the heterostructured silica catalysts. The catalysts of the present invention can include a transition metal, an alkaline earth metal oxide, and silica, wherein the transition metal, the alkaline earth metal from the metal oxide thereof, and silicon (Si) from silica are each present in the crystal lattice structure of the catalyst.

The catalytically active material used to prepare the heterostructured silica catalysts of the present invention includes one or more catalytically active metals. The crystal lattice structure of the catalyst can contain one metal (i.e., monometallic), two metals (i.e., bimetallic), three metals (i.e., trimetallic), four metals (i.e., tetrametallic) or more metals. In one embodiment, the catalytic metal is a transition metal. An amount of transition metal can depend inter alia on the desired activity of the catalyst. Non-limiting examples of transition metal include scandium (Sc), yttrium (Y), lanthanum (La), titanium (Ti), zirconium (Zr), hafnium (Hf), vanadium (V), niobium (Nb), tantalum (Ta), chromium (Cr), molybdenum (Mo), tungsten (W), manganese (Mn), technetium (Tc), rhenium (Re), iron (Fe), ruthenium (Ru), osmium (Os), cobalt (Co), rhodium (Rh), iridium (Ir), nickel (Ni), palladium (Pd), copper (Cu), silver (Ag), and gold (Au). Preferably the transition metal is one or more of iron (Fe), nickel (Ni), copper (Cu), zinc (Zn), aluminum (Al), zirconium (Zr), or titanium (Ti), with iron (Fe) being preferred. The amount of transition metal comprised in the heterostructured silica catalyst can include 0.01 to 20 wt. % or 0.1 to 10 wt. % and all values and ranges there between. For example, the catalyst can include about 0.2, 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, or 9.9 wt. % of the transition metal based on the total weight of the catalyst. Transition metals and corresponding stable derivatives/precursors thereof (e.g., halides, oxides, etc.) can be purchased from commercial manufactures such as Sigma-Aldrich®, USA.

The heterostructured silica catalysts of the present invention also include an alkaline earth metal oxide. The alkaline earth metal oxide may be inert or be able to participate in catalytic reactions. The alkaline earth metal oxide can be one or more of magnesium oxide (MgO), calcium oxide (CaO), barium oxide (BaO), or strontium (SrO), with magnesium oxide (MgO) being preferred. The amount of alkaline earth metal from the metal oxide thereof comprised in the heterostructured silica catalyst can include 5 to 40 wt. % or 10 to 20 wt. % and all values and ranges there between. For example, the catalyst can include 5, 5.5, 6, 6.5, 7.0, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 30, 30.5, or 40 wt. % based on the total weight of the catalyst. In some instances, the alkaline earth metal oxide can be present in the crystal lattice structure of the catalyst in a weight ratio of silicon to alkaline earth metal from 0.5:1 to 5:1 with 1:1 to 3:1 and all values and ranges there between (e.g., 1.1:1, 1.2:1, 1.3:1, 1.4:1, 1.5:1, 1.6:1, 1.7:1, 1.8:1, 1.9:1, 2.0:1, 2.1:1, 2.2:1, 2.3:1, 2.4:1, 2.5:1, 2.6:1, 2.7:1, 2.8:1, 2.9:1). Alkaline earth metal oxides and corresponding derivatives/precursors thereof (e.g., halides), can be purchased from commercial manufactures such as Sigma-Aldrich®, USA.

Silica or silicon dioxide (i.e., $SiO_2$) is the oxide of silicon that is highly abundant in nature (e.g., quartz). Silica more so than almost any material, exists in many crystalline forms (e.g., polymorphs). Due to a range of robust structure properties and high surface area, silica is often included in catalyst support materials to which active metals are affixed. Great effort has been made to maximize the surface area of a catalyst by increasing distribution over and within the support. The amount of silicon (Si) from silica comprised in the heterostructured silica catalyst can include 10 to 50 wt. % or 20 to 40 wt. % and all values and ranges there between (e.g., 21, 22, 23, 24, 25, 26, 27, 28, 29, 30, 31, 32, 33, 34, 35, 36, 37, 38, or 39 wt. %) of silicon, based on the total weight of the catalyst. A wide range of silicon containing precursors can be used to prepare the heterostructured silica catalysts of the present invention. In particular aspects, the sources of silicon can be derived from organic compounds that readily provide soluble sources of silicon in a template reaction. In coordination chemistry, a template reaction is a ligand-based reaction that occurs between two or more adjacent coordination sites on a metal center. Providing silicon under templating conditions effects the pre-organization provided by the coordination sphere which can result in significant modification of physical/chemical/electronic properties of the template complex formed which can have profound effects on the resultant crystal morphology (e.g., size, shape, dispersion, surface area, distribution) of the resultant heterostructured silica catalyst formed. Preferably the organic source of silicon that be used to form the silica comprised in the heterostructured silica catalysts include tetraalkyl orthosilicates. Tetraalkyl orthosilicate derivatives (e.g., tetraethyl orthosilicate (TEOS) can be purchased from commercial manufactures such as Sigma-Aldrich®, USA.

B. Methods of Making the Catalysts

The catalysts of the present invention can be prepared by using the following non-limiting steps. In the method of the invention orthosilicate can be added to heated aqueous alkaline earth metal salt (e.g., $MgCl_2$). Under these conditions, orthosilicate can be converted into polycondensed silica with an external network of alkaline earth metal atoms (e.g., Mg) along with an organic phase (e.g., ethyl moiety). A transition metal salt (e.g., iron citrate) can then be added in solid form. The transition metal salt dissolves slowly to allow the transition metal (e.g., iron) to network with the existing solution in a regular systematic pattern. This regular patterned solution can then be precipitated by means of precipitating agent to keep the heterostructure intact. Upon drying, interstitial water can be removed producing a uniformly shaped material.

Step 1 of the method can include subjecting an aqueous solution comprising an alkaline earth metal precursor and a silicon containing organic template (e.g., tetraalkyl orthosilicate) to conditions sufficient to form polycondensed silica having an external network of alkali earth metal atoms. The molar ratio of tetraalkyl orthosilicate to alkaline earth metal precursor can be 0.5:1 to 6:1, preferably 1:1 to 4:1 and all ranges and values there between (e.g., 1.1:1, 1.2:1, 1.3:1, 1.4:1, 1.5:1, 1.6:1, 1.7:1, 1.8:1, 1.9:1, 2.0:1, 2.1:1, 2.2:1, 2.3:1, 2.4:1, 2.5:1, 2.6:1, 2.7:1, 2.8:1, 2.9:1, 3.0:1, 3.1:1, 3.2:1, 3.3:1, 3.4:1, 3.5:1, 3.6:1, 3.7:1, 3.8:1, or 3.9:1). Non-limiting examples of the alkaline earth metal precursor include magnesium fluoride ($MgF_2$), magnesium chloride ($MgCl_2$), magnesium bromide ($MgBr_2$), magnesium iodide ($MgI_2$), calcium fluoride ($CaF_2$), calcium chloride ($CaCl_2$), calcium bromide ($CaBr_2$), calcium iodide ($CaI_2$), barium fluoride ($BaF_2$), barium chloride ($BaCl_2$), barium bromide ($BaBr_2$), barium iodide ($BaI_2$), strontium fluoride ($SrF_2$), strontium chloride ($SrCl_2$), strontium bromide ($SrBr_2$), strontium iodide ($SrI_2$), with $MgCl_2$ being preferred. Non-limiting examples of tetraalkyl orthosilicates or alkoxy silanes include tetramethyl orthosilicate (TMOS), tetraethyl orthosilicate (TEOS), tetrapropoxysilane, tetraisopropoxysilane, tetrabutoxysilane, tetraisobutoxysilane, tetrakis(methoxyethoxy)silane, tetrakis(methoxypropoxy)silane, tetrakis(ethoxyethoxy)silane, tetrakis(methoxyethoxyethoxy)silane, trimethoxyethoxysilane, dimethoxydiethoxysilane, triethoxymethoxysilane, tetra-(4-methyl-2-pentoxy)silane, and tetra-(2-ethylhexoxy)silane. Additional examples of tetrafunctional silanes with acyloxy groups include tetraacetoxyoxysilane, silicon tetrapropionate and silicon tetrabutyrate. Preferably the tetraalkyl orthosilicate is TEOS. The aqueous solution can include from 10 to 100 vol. % water and all ranges and values there between (e.g., 10, 20, 30, 40, 50, 60, 70, 80, 90 vol. %) The aqueous solution can also include an alcohol. Non-limiting examples of alcohols include methanol, ethanol, propanol, isopropanol, butanol, or glycerol to name a few, preferably the alcohol is ethanol, propanol, butanol, or mixtures thereof. The aqueous solution of alkaline earth metal precursor and an tetraalkyl orthosilicate can be mixed together using suitable mixing equipment and heated to a temperature of room temperature to 90° C., preferably 50° C. to 60° C., and all values and ranges there between (e.g., 51, 52, 53, 54, 55, 56, 57, 58, 59° C.). In other aspects, an alkaline earth metal precursor solution can first be formed. The alkaline earth metal precursor solution can be heated to a temperature ranging from room temperature to 95° C., preferably from 40 to 70° C. and all ranges and values there between (e.g., 41, 42, 43, 44, 45, 46, 47, 48, 49, 50, 51, 52, 53, 54, 55, 56, 57, 58, 59, 60, 61, 62, 63, 64, 65, 66, 67, 68, or 69° C.) followed by adding the tetraalkyl orthosilicate to the solution. In particular aspects, a mixture of TEOS and $MgCl_2$ results in the formation of a polycondensed support material containing uniform single crystal structure including heterostructures of silica magnesia within an organic template.

Step 2 of the method can include adding a transition metal precursor material to the aqueous solution including polycondensed silica having an external network of alkali earth metal atoms under conditions to incorporate transition metal atoms into the polycondensed silica. The molar ratio of alkaline earth metal precursor to transition metal precursor can be 5:1 to 50:1, preferably 20:1 to 30:1 and all ranges and values there between Non-limiting ratios include about 20.1:1, 20.5:1, 21.0:1, 21.5:1, 22.0:1, 22.5:1, 23.0:1, 23.5:1, 24.0:1, 24.5:1, 25.0:1, 25.5:1, 26:1, 26.5:1, 27.0:1, 27.5:1, 28.0:1, 28.5:1, 29.0:1, 29.5:1, or 30:1. The transition metal precursor can include ferric citrate, nickel citrate, copper citrate, zinc citrate, aluminum citrate, zirconium citrate, or titanium citrate. After adding the transition metal precursor, the aqueous mixture can be stirred (e.g., vigorously) for an appropriate amount of time to incorporate the transition metal precursor. The appropriate amount of time can include from 30 minutes to overnight (e.g., approximately 12 hours), 1 hour to 6 hours, preferably about 2 hours.

Step 3 of the method can include forming a solid material from the polycondensed silica. In some instances, the solid material can be obtained by adding a precipitating agent. The precipitating agent can be one or more of ammonium hydroxide ($NH_4OH$), ammonium carbonate [$(NH_4)_2CO_3$], ammonium bicarbonate ($NH_4HCO_3$), sodium carbonate ($Na_2CO_3$), potassium carbonate ($K_2CO_3$), sodium bicarbonate ($NaHCO_3$), or potassium bicarbonate ($KHCO_3$). Preferably the precipitating agent is $NH_4OH$. In other instances, the precipitating agent can have a concentration from 1M to 10M of precipitation agent in water. After adding the precipitating agent, the aqueous mixture can be stirred (e.g., vigorously) for an appropriate amount of time to form the solid material. The appropriate amount of time can include from 30 minutes to overnight (e.g., approximately 12 hours), 1 hour to 6 hours, preferably about 2 hours.

Step 4 of the method can include drying and calcining the solid material to form a heterostructured silica catalyst comprising a transition metal, an alkaline earth metal oxide, and silica, wherein the transition metal, the alkaline earth metal from the metal oxide thereof, and silicon (Si) from silica are each present in the crystal lattice structure of the catalyst. After the solid material is formed by precipitation, it can be collected by filtration, washed with hot water, and dried overnight at a temperature of 100 to 150° C., preferably 130° C. In certain instances (e.g., when the transition metal is iron) after drying, the material can be treated with an oxidant (e.g., $H_2O_2$) under stirring conditions for a period of time (e.g., 30 minutes to 2 hours, preferably approximately 1 hour) followed by isolation by filtration and drying. Drying can include a time of 2 hours to overnight, preferably approximately 4 hours at a temperature of 100 to 150° C., preferably 130° C. Further calcination of the dried solid material can include heating at a temperature from 250 to 800° C. and all ranges and values there between preferably 400 to 500° C. Preferably, calcination is employed under temperature ramping conditions (e.g., 3° C./minute) to a hold temperature (e.g., 450° C.) and holding for 3 to 7 hours, preferably 5 hours in air to form the final heterostructured silica catalysts.

The morphology, structure, and quality of the heterostructured silica catalysts of the present invention can be evaluated using techniques, such as, but not limited to, scanning electron microscopy (SEM), high-resolution transmission electron microscopy (HRTEM), Raman spectroscopy, UV-VIS, optical reflectivity, optical microscopy, low-energy electron microscopy (LEEM), low-energy diffraction (LEED), atomic force microscopy (AFM), transmission electron microscopy (TEM), scanning tunnelling microscopy (STM), photoelectron microscopy (PES), angle-resolved photoelectron spectroscopy (ARPES), photoemission electron microscope (PEEM), energy dispersive X-ray spectroscopy (EDS, EDX, or XEDS), X-ray photoelectron spectroscopy (XPS), Image J data analysis software, reflection high-energy electron diffraction (RHEED), or microscope-based videography.

C. Hydrocarbon Production

1. Methods and Systems

The heterostructured silica catalyst of the present invention can be used to catalyze a chemical reaction, such as the hydrogenation of carbon monoxide. In non-limiting embodiments, the hydrogenation of carbon monoxide includes the conversion of synthesis gas (e.g., gas that include $H_2$ and CO) to carbon dioxide, methane, olefins (e.g., ethylene, propylene, and butylenes), and and/or paraffins (e.g., $C_2$+ alkanes). Conditions sufficient for production include temperature, time, syngas ratio and concentration, space velocity, and pressure. The temperature range for hydrocarbon production may range from about 200° C. to 500° C., preferably 250° C. to 350° C. A weighted hourly space velocity (WHSV) of syngas higher than 1000 $h^{-1}$ can be used, preferably between 1000 and 10,000 $h^{-1}$, most preferably approximately 1875 $h^{-1}$. The conversion of syngas can be carried out at a pressure from 0 to 15 bar, preferably approximately 5 bar, or at atmospheric pressure. The conditions for hydrocarbon production may be varied based on the type of the reactor. Prior to using the heterostructured silica catalyst of the present invention, the catalysts can be activated by ramping 3° C./minute to 350° C. and holding for 16 hour under 50:50 $H_2/N_2$ flow (e.g., WHSV: 3600 $h^{-1}$).

The reaction of the methods and system disclosed herein can occur in any type of reactor. Non-limiting examples of reactors include a high throughput fixed bed flow reactor setup housed in a temperature controlled system fitted with regulators to maintain pressure during the reaction. It is also envision the method and systems may also include the ability to regenerate used/deactivated catalyst in a continuous process such as in a fluidized bed reactor. The method and system can further include collecting or storing the produced hydrocarbon product along with using the produced hydrocarbon product to produce downstream petrochemical and/or polymer products. Reaction products of the reactions can be analyzed by online GC analysis for purity.

Figure 1:
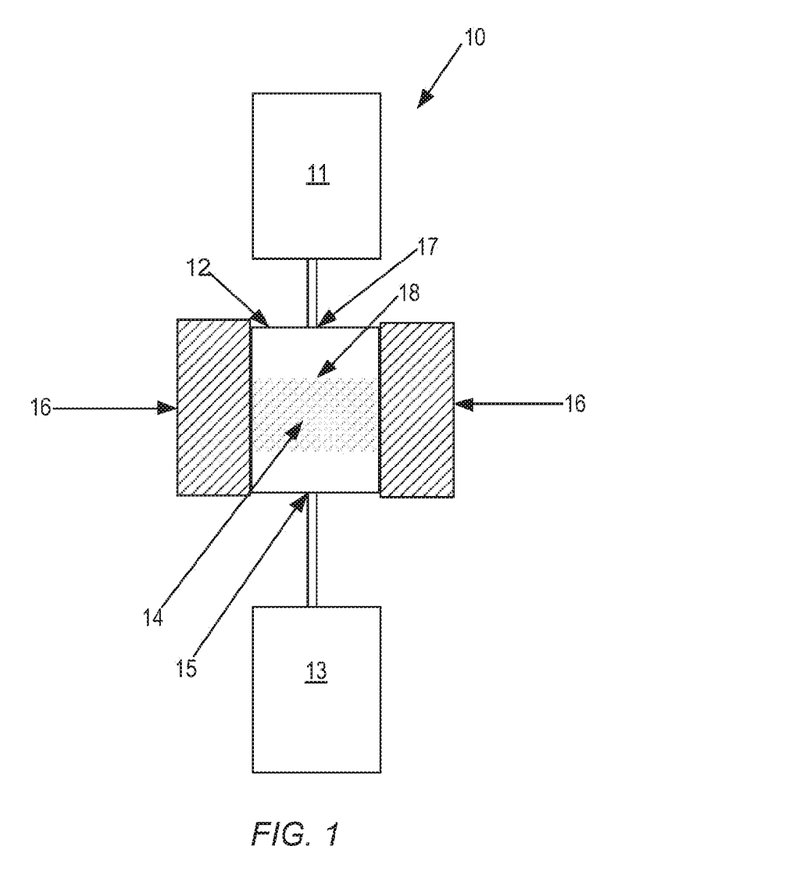
FIG. 1 depicts a system for the hydrogenation of carbon monoxide.

Referring to FIG. 1, a system 10 is illustrated, which can be used to convert syngas to hydrocarbon products with the heterostructured silica catalysts of the present invention. The system 10 can include a syngas source 11, a reactor 12, and a collection device 13. The syngas source 11 can be configured to be in fluid communication with the reactor 12 via an inlet 17 on the reactor. In a non-limiting aspect, one or more inlets can be present that can deliver syngas in a single feed as a $H_2$/CO mixture or separately via multiple inlets (not shown). As explained above, the syngas source can be configured such that it regulates the amount of syngas feed entering the reactor 12. The reactor 12 can include a reaction zone 18 having the heterostructured silica catalyst 14 of the present invention (MHH—$SiO_2$ catalyst). The amounts of the syngas feed 11 and the catalyst 14 used can be modified as desired to achieve a given amount of product produced by the system 10. The reactor 12 can include an outlet 15 for products produced in the reaction zone 18. The products produced can include carbon dioxide, methane, olefins (e.g., ethylene, propylene, and butylenes), and/or paraffins (e.g., $C_2+$ alkanes). The collection device 13 can be in fluid communication with the reactor 12 via the outlet 15. Both the inlet 17 and the outlet 15 can be open and closed as desired. The collection device 13 can be configured to store, further process, or transfer desired reaction products (e.g., olefins) for other uses. Still further, the system 10 can also include a heating source 16. The heating source 16 can be configured to heat the reaction zone 18 to a temperature sufficient (e.g., 250 to 350° C.) to convert syngas to hydrocarbon products. A non-limiting example of a heating source 16 can be a temperature controlled furnace. Additionally, any unreacted syngas can be recycled and included in the syngas feed to further maximize the overall conversion of syngas to hydrocarbon products. Further, certain products can be separated by known processes in the art and used in other processes to produce commercially valuable chemicals. This increases the efficiency and commercial value of the syngas conversion process of the present invention.

2. Reactants and Products

Carbon monoxide (CO) gas and hydrogen ($H_2$) gas can be obtained from various sources. The CO can be obtained from streams coming from other chemical processes, like partial oxidation of carbon-containing compounds, iron smelting, photochemical process, syngas production, reforming reactions, and/or various forms of combustion. $H_2$ can be obtain from streams coming from other chemical processes, like water splitting (e.g., photocatalysis, electrolysis, or the like), syngas production, ethane cracking, methanol synthesis, or conversion of methane to aromatics. The molar ratio of $H_2$/CO in the reactant stream can be 1 or more. In some embodiments, the $H_2$/CO molar ratio can be from 1 to 10, preferably approximately 2. In some examples, the remainder of the reactant gas stream can include another gas or gases provided the gas or gases are inert, such as argon (Ar), nitrogen ($N_2$), or methane and further provided that they do not negatively affect the reaction. All possible percentages of CO plus $H_2$ plus inert gas in the current embodiments can have the described $H_2$/CO ratios herein. Preferably, the reactant mixture is highly pure and devoid of water or steam. In some embodiments, the feed gases can be dried prior to use (e.g., pass through a drying media) or contain a minimal amount of water or no water at all.

The process of the present invention can produce a product stream that includes a mixture of carbon dioxide, methane, olefins (e.g., ethylene, propylene, and butylenes), and/or paraffins (e.g., $C_2+$ alkanes). In particular instances, the carbon monoxide conversion can be 70 to 78% at 300° C., 67 to 80% at 325° C., and 14 to 53% at 350° C. The selectivity of methane can be 11 to 28%, the selectivity of olefins can be 24 to 41%, the selectivity of paraffins can be 13 to 21%, and the selectivity of carbon dioxide can be 13 to 41%, based on a reaction mass balance of 95±5%.

EXAMPLES

The present invention will be described in greater detail by way of specific examples. The following examples are offered for illustrative purposes only, and are not intended to limit the invention in any manner. Those of skill in the art will readily recognize a variety of noncritical parameters, which can be changed or modified to yield essentially the same results.

Aqueous magnesium chloride (1M), tetraethyl orthosilicate (98%, TEOS), ferric citrate (16.5 to 18.5 wt %, based on total weight of solution), aqueous ammonium hydroxide (1M, 3M, 5M, and 7M), and aqueous hydrogen peroxide (15%) were used without further purification.

Example 1

Preparation of a MHH—$SiO_2$ Material $MgCl_2$ (1M, 20 mL) and distilled $H_2O$ ("$dH_2O$", 80 mL) were added to a beaker and stirred vigorously at 50 to 60° C. TEOS (10.4 g) was then added dropwise followed by ferric citrate crystals (0.25 g), and stirring was continued for 2 hours. $NH_4OH$ (1M, 100 mL) was then added and the mixture was vigorously stirred for another 2 hours. The resulting solid material was collected by filtration, washed with hot water, and dried overnight at 130° C. After drying, the material was immersed in $H_2O_2$ (15%, 50 ml) for 1 hour followed by filtration and drying for 4 hours at 130° C. The material was then calcined ramping 3° C./minute to 450° C. and holding for 5 hours in air before use as support in catalyst preparations.

Example 2

Preparation of a MHH—$SiO_2$ Material $MgCl_2$ (1M, 20 mL) and $dH_2O$ (80 mL) were added to a beaker and stirred vigorously at 50 to 60° C. TEOS (10.4 g) was then added dropwise followed by ferric citrate crystals (0.25 g) and stirring was continued for 2 hours. $NH_4OH$ (3M, 100 mL) was then added and the mixture was vigorously stirred for another 2 hours. The resulting solid material was collected by filtration, washed with hot water, and dried overnight at 130° C. After drying, the material was immersed in $H_2O_2$ (15%, 50 ml) for 1 hour followed by filtration and drying for 4 hours at 130° C. The material was then calcined ramping 3° C./minute to 450° C. and holding for 5 hours in air before use as support in catalyst preparations.

Example 3

Preparation of a MHH—$SiO_2$ Material $MgCl_2$ (1M, 20 mL) and $dH_2O$ (80 mL) were added to a beaker and stirred vigorously at 50 to 60° C. TEOS (10.4 g) was then added dropwise followed by ferric citrate crystals (0.25 g) and stirring was continued for 2 hours. $NH_4OH$ (5M, 100 mL) was then added and the mixture was vigorously stirred for another 2 hours. The resulting solid material was collected by filtration, washed with hot water, and dried overnight at 130° C. After drying, the material was immersed in $H_2O_2$ (15%, 50 ml) for 1 hour followed by filtration and drying for 4 hours at 130° C. The material was then calcined ramping 3° C./minute to 450° C. and holding for 5 hours in air before use as support in catalyst preparations.

Example 4

Preparation of a MHH—$SiO_2$ Material $MgCl_2$ (1M, 20 mL) and $dH_2O$ (80 mL) were added to a beaker and stirred vigorously at 50 to 60° C. TEOS (10.4 g)

was then added dropwise followed by ferric citrate crystals (0.25 g) and stirring was continued for 2 hours. NH$_4$OH (7M, 100 mL) was then added and the mixture was vigorously stirred for another 2 hours. The resulting solid material was collected by filtration, washed with hot water, and dried overnight at 130° C. After drying, the material was immersed in H$_2$O$_2$ (15%, 50 ml) for 1 hour followed by filtration and drying for 4 hours at 130° C. The material was then calcined ramping 3° C./minute to 450° C. and holding for 5 hours in air before use as support in catalyst preparations.

Example 5

Preparation of a MHH—SiO$_2$ Material

MgCl$_2$ (1M, 30 mL) and dH$_2$O (70 mL) were added to a beaker and stirred vigorously at 50 to 60° C. TEOS (10.4 g) was then added dropwise followed by ferric citrate crystals (0.25 g) and stirring was continued for 2 hours. NH$_4$OH (1M, 100 mL) was then added and the mixture was vigorously stirred for another 2 hours. The resulting solid material was collected by filtration, washed with hot water, and dried overnight at 130° C. After drying, the material was immersed in H$_2$O$_2$ (15%, 50 ml) for 1 hour followed by filtration and drying for 4 hours at 130° C. The material was then calcined ramping 3° C./minute to 450° C. and holding for 5 hours in air before use as support in catalyst preparations.

Example 6

Preparation of a MHH—SiO$_2$ Material

MgCl$_2$ (1M, 30 mL) and dH$_2$O (70 mL) were added to a beaker and stirred vigorously at 50 to 60° C. TEOS (10.4 g) was then added dropwise followed by ferric citrate crystals (0.25 g) and stirring was continued for 2 hours. NH$_4$OH (3M, 100 mL) was then added and the mixture was vigorously stirred for another 2 hours. The resulting solid material was collected by filtration, washed with hot water, and dried overnight at 130° C. After drying, the material was immersed in H$_2$O$_2$ (15%, 50 ml) for 1 hour followed by filtration and drying for 4 hours at 130° C. The material was then calcined ramping 3° C./minute to 450° C. and holding for 5 hours in air before use as support in catalyst preparations.

Example 7

Preparation of a MHH—SiO$_2$ Material

MgCl$_2$ (1M, 30 mL) and dH$_2$O (70 mL) were added to a beaker and stirred vigorously at 50 to 60° C. TEOS (10.4 g) was then added dropwise followed by ferric citrate crystals (0.25 g) and stirring was continued for 2 hours. NH$_4$OH (5M, 100 mL) was then added and the mixture was vigorously stirred for another 2 hours. The resulting solid material was collected by filtration, washed with hot water, and dried overnight at 130° C. After drying, the material was immersed in H$_2$O$_2$ (15%, 50 ml) for 1 hour followed by filtration and drying for 4 hours at 130° C. The material was then calcined ramping 3° C./minute to 450° C. and holding for 5 hours in air before use as support in catalyst preparations.

Example 8

Preparation of a MHH—SiO$_2$ Material

MgCl$_2$ (1M, 30 mL) and dH$_2$O (70 mL) were added to a beaker and stirred vigorously at 50 to 60° C. TEOS (10.4 g) was then added dropwise followed by ferric citrate crystals (0.25 g) and stirring was continued for 2 hours. NH$_4$OH (7M, 100 mL) was then added and the mixture was vigorously stirred for another 2 hours. The resulting solid material was collected by filtration, washed with hot water, and dried overnight at 130° C. After drying, the material was immersed in H$_2$O$_2$ (15%, 50 ml) for 1 hour followed by filtration and drying for 4 hours at 130° C. The material was then calcined ramping 3° C./minute to 450° C. and holding for 5 hours in air before use as support in catalyst preparations.

Example 9

Preparation of a MHH—SiO$_2$ Material

MgCl$_2$ (1M, 20 mL) and dH$_2$O (80 mL) were added to a beaker and stirred vigorously at 50 to 60° C. TEOS (21 g) was then added dropwise followed by ferric citrate crystals (0.25 g) and stirring was continued for 2 hours. NH$_4$OH (1M, 100 mL) was then added and the mixture was vigorously stirred for another 2 hours. The resulting solid material was collected by filtration, washed with hot water, and dried overnight at 130° C. After drying, the material was immersed in H$_2$O$_2$ (15%, 50 ml) for 1 hour followed by filtration and drying for 4 hours at 130° C. The material was then calcined ramping 3° C./minute to 450° C. and holding for 5 hours in air before use as support in catalyst preparations.

Example 10

Preparation of a MHH—SiO$_2$ Material

MgCl$_2$ (1M, 20 mL) and dH$_2$O (80 mL) were added to a beaker and stirred vigorously at 50 to 60° C. TEOS (21 g) was then added dropwise followed by ferric citrate crystals (0.25 g) and stirring was continued for 2 hours. NH$_4$OH (3M, 100 mL) was then added and the mixture was vigorously stirred for another 2 hours. The resulting solid material was collected by filtration, washed with hot water, and dried overnight at 130° C. After drying, the material was immersed in H$_2$O$_2$ (15%, 50 ml) for 1 hour followed by filtration and drying for 4 hours at 130° C. The material was then calcined ramping 3° C./minute to 450° C. and holding for 5 hours in air before use as support in catalyst preparations.

Example 11

Preparation of a MHH—SiO$_2$ Material

MgCl$_2$ (1M, 20 mL) and dH$_2$O (80 mL) were added to a beaker and stirred vigorously at 50 to 60° C. TEOS (21 g) was then added dropwise followed by ferric citrate crystals (0.25 g) and stirring was continued for 2 hours. NH$_4$OH (5M, 100 mL) was then added and the mixture was vigorously stirred for another 2 hours. The resulting solid material was collected by filtration, washed with hot water, and dried overnight at 130° C. After drying, the material was immersed in H$_2$O$_2$ (15%, 50 ml) for 1 hour followed by filtration and drying for 4 hours at 130° C. The material was then calcined ramping 3° C./minute to 450° C. and holding for 5 hours in air before use as support in catalyst preparations.

Example 12

Preparation of a MHH—SiO$_2$ Material

MgCl$_2$ (1M, 20 mL) and dH$_2$O (80 mL) were added to a beaker and stirred vigorously at 50 to 60° C. TEOS (21 g) was then added dropwise followed by ferric citrate crystals (0.25 g) and stirring was continued for 2 hours. NH$_4$OH (7M, 100 mL) was then added and the mixture was vigorously stirred for another 2 hours. The resulting solid material was collected by filtration, washed with hot water, and dried overnight at 130° C. After drying, the material was immersed in H$_2$O$_2$ (15%, 50 ml) for 1 hour followed by filtration and drying for 4 hours at 130° C. The material was then calcined ramping 3° C./minute to 450° C. and holding for 5 hours in air before use as support in catalyst preparations.

Example 13

Catalyst Characterization

The catalyst from Examples 1, 3 and 6 was characterized using EDX.

TABLE 1

EDX analysis of selected samples.

| Example | O | Mg | Si | Fe | Si/Mg |
|---|---|---|---|---|---|
| Example 3 | | | | | |
| Mean | 53.3 | 13.3 | 32.3 | 1.0 | 2.43 |
| Standard | 1.86 | 0.25 | 1.63 | 0.24 | |
| Example 1 | | | | | |
| Mean | 57.3 | 16.5 | 25.3 | 0.8 | 1.53 |
| Standard | 3.11 | 0.33 | 2.52 | 0.31 | |
| Example 6 | | | | | |
| Mean | 60.9 | 16.1 | 22.7 | 0.4 | 1.41 |
| Standard | 1.91 | 0.38 | 1.59 | 0.52 | |

Figure 2:
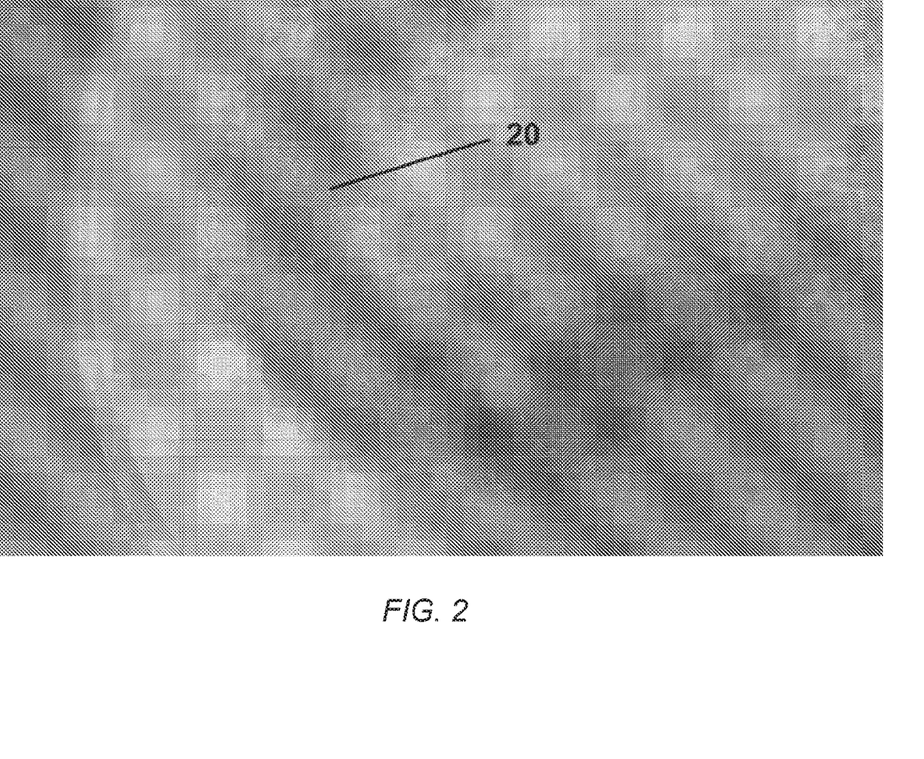
FIG. 2 is an image showing the physical morphology of a filtered support material having uniform single crystal structure.

FIG. 2 depicts an photograph of the catalyst on a filtered support material. As shown in FIG. 2, the catalyst of the present invention had a uniform single crystal structure. Crystals 20 were determined to be heterostructures of silica magnesia having an organic template. Without wishing to be bound by theory, it is believed that once the active metal deposits on the crystals, the organic template dissolved, allowing the metal to reach the support center having systematic pattern to obtain a uniformly designed supported metal catalyst. Elemental composition of the samples determined by EDX are shown in Table 1.

Example 14

Catalyst Activity/Selectivity Evaluation

Figure 3:
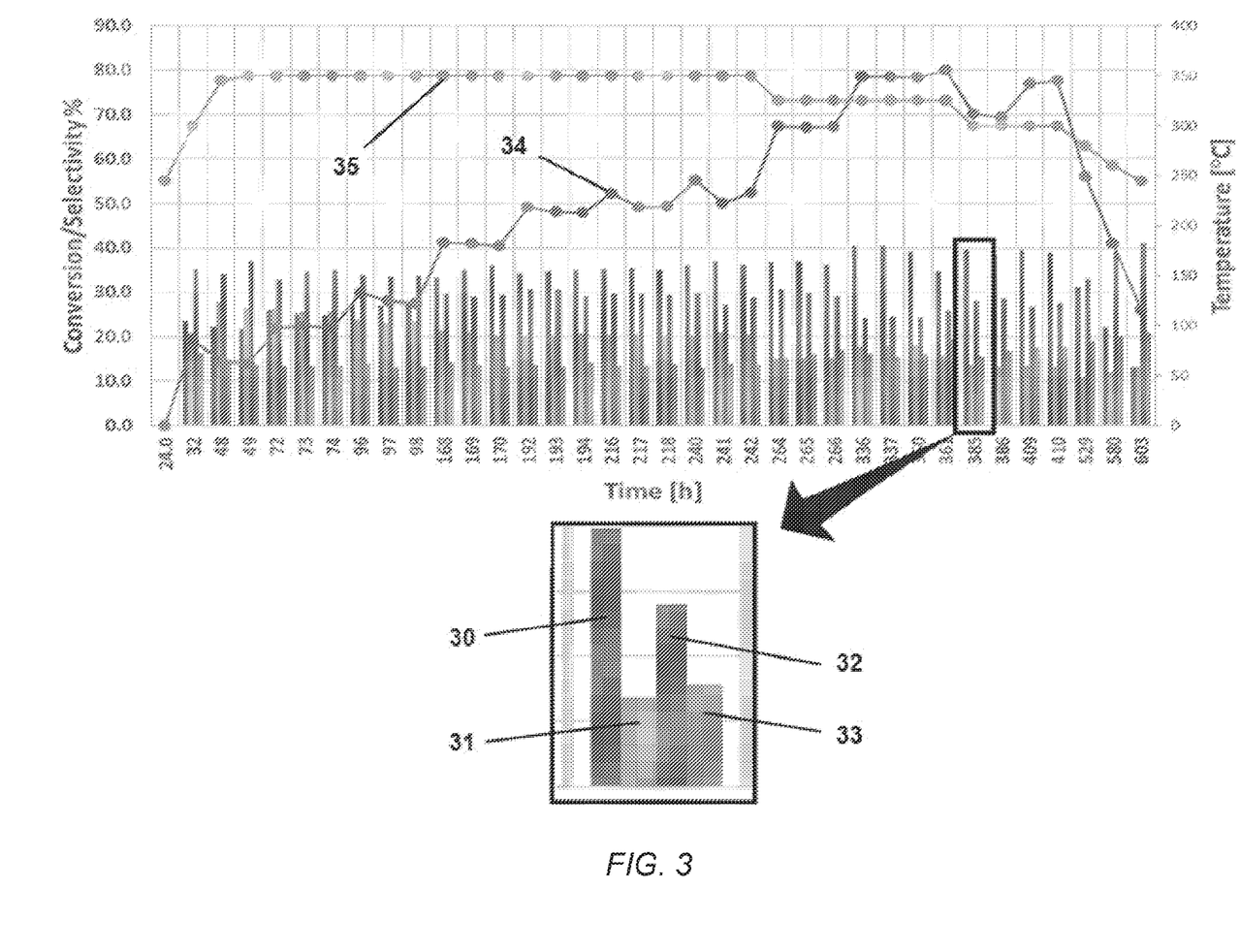
FIG. 3 is a graph showing the activity/selectivity results of a MHH—$SiO_2$ catalyst.

Catalysts were tested for activity, selectivity, as well as short term and long term stability. Prior to activity testing, catalysts were activated by ramping 3° C./minute to 350° C. and holding for 16 hour under 50:50 H$_2$/N$_2$ flow (WHSV: 3600 h$^{-1}$). Catalytic evaluation was carried out in a high throughput fixed bed flow reactor setup housed in a temperature controlled system fitted with regulators to maintain pressure during the reaction. The products of the reactions were analyzed by online GC analysis. The evaluation was carried out under the following conditions unless otherwise mentioned elsewhere; 5 bar, WHSV: 1875 h$^{-1}$, H$_2$/CO ratio of 2. The mass balance of the reactions is calculated to be 95±5%. FIG. 3 depicts a temperature scan of the catalyst of Example 3 for the activity/selectivity evaluation. The exploded view shows which bars represent carbon dioxide 30, methane 31, olefins 32, and paraffins 33 conversion/selectivity data points for each measurement. Carbon monoxide conversion 34 and temperature 35 data points are shown as line graphs. The graph showed the variation in conversion and product selectivities over a duration of 603 hours. The catalyst of Example 3 showed low conversion at low temperature and increased conversion as temperature increased to a maximum at 350° C. On lowering the temperature, the conversion drop was not observed until 300° C., which remains near 80%. Further decrease in temperature produced the usual effect of a conversion drop to 25% at 245° C. The results of FIG. 3 are tabulated in Table 2.

TABLE 2

| Time [h] | Temp. [° C.] | CO Conv. | OC (olefins) | PC2+ (paraffins) | CH$_4$ | CO$_2$ |
|---|---|---|---|---|---|---|
| 24 | 245 | 0 | 0 | 0 | 0 | 0 |
| 32 | 300 | 19.1 | 35 | 16 | 21 | 23 |
| 48 | 345 | 14.5 | 34 | 14 | 28 | 22 |
| 49 | 350 | 13.9 | 37 | 14 | 26 | 22 |
| 72 | 350 | 21.9 | 33 | 13 | 26 | 26 |
| 73 | 350 | 22.4 | 35 | 13 | 26 | 25 |
| 74 | 350 | 21.9 | 35 | 13 | 25 | 25 |
| 96 | 350 | 29.8 | 34 | 14 | 24 | 27 |
| 97 | 350 | 28.1 | 33 | 13 | 23 | 27 |
| 98 | 350 | 27.5 | 34 | 13 | 23 | 28 |
| 168 | 350 | 41.0 | 30 | 14 | 21 | 33 |
| 169 | 350 | 40.9 | 29 | 14 | 21 | 35 |
| 170 | 350 | 40.3 | 29 | 13 | 20 | 36 |
| 192 | 350 | 49.2 | 31 | 14 | 20 | 34 |
| 193 | 350 | 48.1 | 31 | 13 | 20 | 35 |
| 194 | 350 | 47.9 | 29 | 14 | 21 | 35 |
| 216 | 350 | 52.1 | 30 | 13 | 20 | 35 |
| 217 | 350 | 49.2 | 30 | 14 | 20 | 35 |
| 218 | 350 | 49.3 | 29 | 14 | 20 | 35 |
| 240 | 350 | 55.3 | 30 | 13 | 20 | 36 |
| 241 | 350 | 50.0 | 27 | 14 | 21 | 37 |
| 242 | 350 | 52.4 | 29 | 14 | 20 | 36 |
| 264 | 325 | 67.4 | 31 | 15 | 15 | 37 |
| 265 | 325 | 67.1 | 30 | 16 | 15 | 37 |
| 266 | 325 | 67.2 | 29 | 17 | 15 | 36 |
| 336 | 325 | 78.4 | 24 | 16 | 18 | 40 |
| 337 | 325 | 78.5 | 25 | 15 | 18 | 41 |
| 360 | 325 | 78.4 | 24 | 16 | 18 | 39 |
| 361 | 325 | 79.9 | 26 | 20 | 16 | 35 |
| 385 | 300 | 70.1 | 28 | 16 | 14 | 40 |
| 386 | 300 | 69.4 | 29 | 17 | 13 | 38 |
| 409 | 300 | 76.9 | 27 | 17 | 13 | 39 |
| 410 | 300 | 77.6 | 28 | 18 | 13 | 39 |
| 529 | 280 | 56.0 | 33 | 19 | 11 | 31 |
| 580 | 260 | 41.0 | 39 | 20 | 12 | 22 |
| 603 | 245 | 26.0 | 41 | 21 | 13 | 13 |

Unique MHH—SiO$_2$ materials were produced by adopting a well-designed methodology to achieve uniform network distribution of iron stabilized silica magnesia heterostructure. These heterostructured silica have uniform surface morphology and are stable at high temperature for significantly long durations as observed from testing. These materials can have applications in wide variety of industries that use silica as a support material for catalysts.

The invention claimed is:

1. A heterostructured silica catalyst comprising a transition metal, an alkaline earth metal oxide, and silica;
    wherein the heterostructured silica catalyst comprises 0.1 to 10 wt. % of the transition metal, based on the total weight of the catalyst;
    wherein the alkaline earth metal oxide comprises an alkaline earth metal selected from the group consisting of magnesium, calcium, strontium and barium;
    wherein the transition metal comprises a member selected from the group consisting of zinc and zirconium, or combinations thereof;
    wherein the catalyst has a crystal structure;
    wherein the transition metal, the alkaline earth metal from the alkaline earth metal oxide thereof, and silicon (Si) from silica are each present in the crystal lattice structure of the catalyst; and
    wherein the weight ratio of silicon (Si) from silica to alkaline earth metal from the metal oxide thereof is from 1.5:1 to 5:1.

2. The heterostructured silica catalyst of claim 1, wherein the weight ratio of silicon (Si) from silica to alkaline earth metal from the metal oxide thereof is 5:1.

3. The heterostructured silica catalyst of claim 1, wherein the weight ratio of silicon (Si) from silica to alkaline earth metal from the metal oxide thereof is 1.5:1.

4. The heterostructured silica catalyst of claim 3, wherein the transition metal comprises zinc.

5. A heterostructured silica catalyst comprising a transition metal, an alkaline earth metal oxide, and silica;
    wherein the heterostructured silica catalyst comprises 0.1 to 10 wt. % of the transition metal, based on the total weight of the catalyst;
    wherein the catalyst has a crystal structure;
    wherein the transition metal, the alkaline earth metal from the alkaline earth metal oxide thereof, and silicon (Si) from silica are each present in the crystal lattice structure of the catalyst;
    wherein the weight ratio of silicon (Si) from silica to alkaline earth metal from the metal oxide thereof is from 1.5:1 to 5:1; and wherein the transition metal comprises zinc.

6. A heterostructured silica catalyst comprising a transition metal, an alkaline earth metal oxide, and silica;
    wherein the heterostructured silica catalyst comprises 0.1 to 10 wt. % of the transition metal, based on the total weight of the catalyst;
    wherein the catalyst has a crystal structure;
    wherein the transition metal, the alkaline earth metal from the alkaline earth metal oxide thereof, and silicon (Si) from silica are each present in the crystal lattice structure of the catalyst;
    wherein the weight ratio of silicon (Si) from silica to alkaline earth metal from the metal oxide thereof is from 1.5:1 to 5:1; and wherein the transition metal comprises zirconium.

* * * * *